US00PP14517P29

(12) United States Plant Patent
Slaughter et al.

(10) Patent No.: US PP14,517 P2
(45) Date of Patent: Feb. 10, 2004

(54) NECTARINE TREE NAMED 'BURNECTTHIRTEEN'

(50) Latin Name: *Prunus persica*
Varietal Denomination: Burnectthirteen

(75) Inventors: John K. Slaughter, Clovis, CA (US); Timothy J. Gerdts, Kingsburg, CA (US)

(73) Assignee: The Burchell Nursery, Inc., Oakdale, CA (US)

( * ) Notice: Subject to any disclaimer, the term of this patent is extended or adjusted under 35 U.S.C. 154(b) by 57 days.

(21) Appl. No.: 10/349,625

(22) Filed: Jan. 22, 2003

(51) Int. Cl.[7] ..... A01H 5/00
(52) U.S. Cl. ..... Plt./188
(58) Field of Search ..... Plt./188

*Primary Examiner*—Bruce R. Campell
*Assistant Examiner*—Susan B. McCormick
(74) *Attorney, Agent, or Firm*—Wells St. John P.S.

(57) ABSTRACT

A new and distinct variety of nectarine tree (*Prunus persica* sub species *nuciperisica*), and which is denominated varietally as 'Burnectthirteen', and which produces an attractively colored white-fleshed, sub-acid clingstone nectarine, which is mature for harvesting and shipment approximately May 24 to June 4 under ecological conditions prevailing in the San Joaquin Valley of Central California.

1 Drawing Sheet

BACKGROUND OF THE NEW VARIETY

The present invention relates to a new, novel and distinct variety of nectarine tree, *Prunus persica* (subspecies *nuci-persica*), and which has been denominated varietally as 'Burnectthirteen'.

ORIGIN

The present variety of nectarine tree resulted from an on-going program of fruit and nut tree breeding. The purpose of this program is to improve the commercial quality of deciduous fruit and nut varieties and rootstocks by creating and releasing promising new selections of prunus, malus and regia species. To this end we make both controlled and hybrid cross pollinations each year in order to produce seedling populations from which improved progenies are evaluated and selected.

The seedling 'Burnectthirteen' was originated by us from a population of seedlings grown in our experimental orchards located near Fowler, Calif. The seedlings, grown on their own roots, were the result of a controlled cross of the yellow-fleshed 'Crimson Baby' nectarine tree (non-patented), which was used as the seed parent, and the sub-acidic white fleshed nectarine tree, 'Arctic Star' (U.S. Plant Pat. No. 9,332) which was used as the pollen parent. One seedling, which is the present variety, exhibited especially desirable characteristics and was designated as 'E7.043'. This seedling was marked for subsequent observation. After the 1998 fruiting season, the new variety of nectarine tree was selected for advanced evaluation and repropagation.

ASEXUAL REPRODUCTION

Asexual reproduction of this new and distinct variety of nectarine tree was accomplished by budding the new nectarine tree variety to 'Nemaguard' Rootstock (non-patented). This was performed by us in our experimental orchard which is located near Fowler, Calif. Subsequent annual evaluations have shown those asexual reproductions run true to the original tree. All characteristics of the original tree, and its fruit, were established and appear to be transmitted through succeeding asexual propagations. We have observed fruit for the past 4 successive years from approximately 15 propagated trees.

SUMMARY OF THE VARIETY

'Burnectthirteen' is a new and distinct variety of nectarine tree, which is considered of large size, and which has vigorous growth. This new nectarine tree variety is also a regular and productive bearer of relatively large, firm, sub-acidic white fleshed, clingstone fruit, which have good flavor and eating quality. The tree of the present variety displays a chilling requirement of approximately 500 hours. Still further the tree also produces relatively uniformly sized fruit throughout the entire tree. Still further, the fruit have a high degree of red skin coloration, and a firm flesh. In addition to the foregoing, the fruit of this new tree also appears to have good handling and shipping qualities. The 'Burnectthirteen' Nectarine tree bears fruit which are ripe for commercial harvesting and shipment on approximately May 24 to June 4 under the ecological conditions prevailing in the San Joaquin Valley of central California. In relative comparison with the 'Crimson Baby' nectarine tree, which is the seed parent, the present new variety of nectarine tree bears fruit which ripen about 5 to 8 days earlier, and further is white fleshed.

BRIEF DESCRIPTION OF THE DRAWING

The accompanying drawing, which is provided, is a color photograph of the new variety of nectarine tree. It depicts two whole mature fruit, and one mature fruit dissected substantially in the equatorial plane, and viewed from the apical perspective, to reveal the flesh coloration and the stone thereof. The external coloration of the fruit is shown sufficiently matured for harvesting and shipment. Additionally the photograph displays a sample vegetative shoot bearing typical leaves, and a typical stone, with the fleshed removed. The colors in this photograph are as nearly true as is reasonably possible in a color representation of this type. Due to chemical development, processing and printing, the leaves and fruit depicted in these photographs may or may not be accurate when compared to the actual specimens. For this reason, future color references should be made to the referenced color plates (Royal Horticultural Society) and the descriptions provided hereinafter.

DETAILED DESCRIPTION

Referring more specifically to the pomological details of this new and distinct variety of nectarine tree, the following has been observed during the fourth fruiting season under the ecological conditions prevailing at orchards located near the town of Fowler, county of Fresno, state of California. All major color code designations are by reference to The R.H.S. Colour Chart (Fourth Edition) provided by The Royal Horticultural Society of Great Britain. Common color names are also occasionally used.

Tree:

*Size.*—Generally — Considered medium-large as compared to other common commercial nectarine cultivars ripening in the early season of maturity. The tree of the present variety was pruned to a height of approximately 270.0 cm to about 300.0 cm at maturity.

*Vigor.*—Considered vigorous. The present nectarine variety grew from about 159.0 cm to 171.0 cm in height during the first growing season. The new nectarine tree variety was pruned to a height of approximately 150.0 cm during the first dormant season, and primary scaffolds were then selected for the desired tree structure.

*Productivity.*—Productive. Fruit set varies from twice to several times more than the desired crop load. Fruit set is spaced by thinning to develop the remaining fruit into the desired market size. The number of fruit set varies with the prevailing climatic conditions, and cultural practices employed during the bloom period and is therefore not distinctive of this new variety.

*Bearer.*—Regular. Fruit set has been heavy and thinning was necessary during the past 5 years.

*Form.*—Upright, and pruned to a vase shape.

*Density.*—Considered medium dense. It has been discovered that pruning the branches from the center of the tree to obtain a resulting vase shape allows for air movement and appropriate amounts of sunlight to enhance the resulting fruit color and renewal of fruiting wood throughout the tree.

*Hardiness.*—The present tree was grown and evaluated in USDA Hardiness Zone 9. Winter chilling requirements of the new tree are approximately 500 hours below 7.0 degrees C. The variety also appears to be hardy under typical central San Joaquin Valley climatic conditions.

Trunk:

*Diameter.*—Approximately 13.0 cm in diameter when measured at a distance of approximately 15.24 cm above the soil level, at the end of the fifth growing season.

*Bark texture.*—Considered moderately rough, with numerous folds of papery scarfskin being present.

*Lenticels.*—Numerous flat, oval lenticels are present. The lenticels range in size from approximately 4.0 to about 7.0 millimeters in width, and from about 1.0 to about 2.0 millimeters in height.

*Lenticel color.*—Considered an orange brown, (RHS Greyed Orange Group 165 B).

*Bark coloration.*—Variable, but it is generally considered to be gray-brown, (RHS Brown Group 200 D).

Branches:

*Size.*—Considered medium for the variety.

*Diameter.*—Average as compared to other nectarine tree varieties. The branches have a diameter of about 5.5 centimeters when measured during the fifth year following grafting.

*Surface texture.*—Average, and appearing furrowed on wood, which is several years old.

*Crotch angles.*—Primary branches are considered variable between about 44 to 51 degrees from the horizontal axis. This particular characteristic is not considered distinctive of the variety however.

*Current season shoots.*—Surface texture — Substantially glabrous.

*Internode length.*—Approximately 2.4 to about 2.7 cm. This tree characteristic is highly dependent upon plant nutrition, soil quality, pruning and tree care and therefore is not distinctive of the variety.

*Color of mature branches.*—Medium brown, (RHS Greyed Orange 165 A).

*Current seasons shoots.*—Color — Light green, (RHS Yellow Green Group N144 B). The color of new shoot tips is considered a bright and shiny green (RHS Yellow-Green Group 143 B).

Leaves:

*Size.*—Considered medium to large for the species. Leaf measurements have been secured from vigorous, upright, current-season growth taken at approximately mid-shoot.

*Leaf length.*—Approximately 142.0 to 158.0 millimeters.

*Leaf width.*—Approximately 37.0 to about 42.0 millimeters.

*Leaf base shape.*—Slightly oblique relative to the leaf longitudinal axis.

*Leaf form.*—Lancelolate.

*Leaf tip form.*—Acuminate.

*Color.*—Upper Leaf Surface — Dark green, (approximately RHS Green Group 136 B).

*Leaf texture.*—Glabrous.

*Color.*—Lower Leaf Surface — Medium green, (RHS Green Group 137 A).

*Leaf venation.*—Pinnately veined.

*Mid-vein.*—Color — Light green, (RHS Green Group 143 C).

*Leaf margins.*—Slightly undulating. Form — Considered crenate, occasionally doubly crenate. Uniformity — Considered generally uniform.

*Leaf petioles.*—Size — Considered medium-long. Length — About 7.0 to about 10.0 mm. Diameter — About 2.0 to about 2.5 mm. Color — Pale green, (RHS Yellow Green Group 145 A).

*Leaf glands.*—Size — About 1.0 mm in height and about 2.0 mm in width. Number — Generally one per side, occasionally two per side. Type — Reniform, and considered reasonably unappressed relative to the petiole margin. The leaf glands are considered moderately small. Color — Orange brown, (RHS Greyed Brown Group N199 D).

*Leaf stipules.*—Size — Average for the variety. Number — Typically 2 per leaf bud, and up to 6 per shoot tip. Form — Lanceolate in form, and having a serrated margin. Color — Green, (RHS Yellow Green Group 145 A) when young, but graduating to a brown color, (RHS Greyed Orange group 166 C) with advancing senescence. The stipules are considered to be early deciduous.

Flowers:

*Flower buds.*—Generally — The floral buds, depending upon the stage of development are approximately 7.0 millimeters wide; and about 11.0 millimeters long; conic in form; and slightly appressed relative to the bearing shoot.

*Flower buds.*—Color — The bud scales are reddish-brown, (approximately RHS Greyed Purple Group 183 B). The buds are considered hardy under typical central San Joaquin Valley climatic conditions.

*Hardiness.*—No winter injury has been noted during the last several years of evaluation in the central San Joaquin Valley. The current variety has not been intentionally subjected to drought or heat stress and therefore this information is not available.

*Date of first bloom.*—Feb. 22, 2002.

*Blooming time.*—Considered early mid-season in relative comparison to other commercial nectarine cultivars grown in the central San Joaquin Valley. Date of full bloom was observed on Feb. 27, 2002. The date of bloom varies slightly with the prevailing climatic conditions and cultural practices.

*Duration of bloom.*—Approximately 10 days. This characteristic varies slightly with the prevailing climatic conditions.

*Flower type.*—The variety is considered to have a showy type flower.

*Flower size.*—Flower diameter at full bloom is approximately 41.0 to about 43.0 millimeters.

*Bloom quantity.*—Considered very abundant.

*Flower bud frequency.*—Normally 1 to 2 flower buds appear per node. Rarely 3 buds per node may be observed.

*Petal size.*—Generally — Considered large for the species. Length — Approximately 19.0 to about 21.0 millimeters. Width — Approximately 18.0 to about 21.0 millimeters.

*Petal form.*—Rotund.

*Petal count.*—Generally 5. Occasionally individual flower pedal counts are doubled.

*Petal texture.*—Glabrous.

*Petal color.*—Light pink, (RHS Red Purple Group 62 C) to a medium pink, (RHS Red Purple Group 58 D).

*Fragrance.*—Slight.

*Petal claw.*—Form — The petal claw is considered truncate in shape, and has a large size when compared to other varieties. Length — Approximately 8.0 to about 10.0 millimeters. Width — Approximately 9.0 to about 11.0 millimeters.

*Petal margins.*—Generally considered variable, from nearly smooth, to moderately undulate.

*Petal apex.*—Generally — The petal apices appear entire and without an apical groove.

*Flower pedicel.*—Length — Considered medium-long, and having an average length of approximately 3.0 to about 4.0 millimeters. Diameter — Considered average, approximately 2.0 millimeters. Color — A reddish brown, (RHS Greyed Purple Group 183 C).

*Floral nectaries.*—Color — A pale green, (RHS Yellow Green Group 153 D).

*Calyx.*—Surface Texture — Generally glabrous. Color — A dull red, (approximately RHS Greyed Purple Group 183 A).

*Sepals.*—Surface Texture — The surface has a short, fine pubescent texture. Size — Average, and ovate in form. Color — A dark reddish purple, (approximately RHS Greyed Purple Group 183 B).

*Anthers.*—Generally — Large in size. Color — Reddish purple, (approximately RHS Greyed Purple Group 183 B).

*Pollen production.*—Pollen is abundant, and has a yellow color, (approximately RHS Yellow Group 12 A).

*Filaments.*—Size — Variable in length, approximately 16.0 to 19.0 millimeters. Color — Considered pink, (RHS Red Purple Group 62 B).

*Pistil.*—Number — Usually 1, occasionally 2. Generally — Average in size. Length — Approximately 16.0 to about 19.0 millimeters including the ovary. Color — Considered a very pale green, (approximately RHS Yellow Green Group 149 D). Surface Texture — The variety has a long glabrous pistil.

Fruit:

*Maturity when described.*—Firm ripe condition (shipping ripe). Date of first picking — May 24, 2002. Date of last picking — Jun. 4, 2002. The date of harvest varies slightly with prevailing climatic conditions.

*Size.*—Generally — Considered relatively large, and uniform.

*Average cheek diameter.*—Approximately 68.0 to about 74.0 millimeters.

*Average axial diameter.*—Approximately 69.0 to about 73.0 millimeters.

*Typical weight.*—Approximately 205.0 grams. This characteristic is highly dependent upon cultural practices and therefore is not particularly distinctive of this new variety.

*Fruit form.*—Generally — Rounded. The fruit is generally uniform in its symmetry.

*Fruit suture.*—Shallow, and extending from the base to the apex. No apparent callousing or stitching exists along the suture line.

*Suture.*—Color — The background color appears to be the same as the blush color, that is, graduating from a light red (approximately RHS Red Group 44 A) to a dark red purple, (approximately RHS Greyed Purple Group 187 A).

*Ventral surface.*—Form — Slightly indented.

*Apex.*—Rounded.

*Base.*—Retuse.

*Stem cavity.*—Rounded and relatively shallow. The average depth of the stem cavity is about 1.55 cm. The average width of the stem cavity is about 1.94 cm.

*Fruit skin.*—Thickness — Considered medium in thickness, and tenacious to the flesh. Texture — Short, fine, and glabrous. Taste — Non-astringent. Tendency to crack — Not observed. Occasional russeting has been observed.

*Color.*—Blush Color — This red blush color is variable from a reddish orange, (approximately RHS Red Group 44 A) to a dark red, (approximately RHS Greyed Purple Group 187 A). The blush color ranges from about 75% to about 95% of the fruit surface depending upon the sunlight exposure and prevailing growing conditions. Ground Color — Generally a light yellow, (approximately RHS White Group 155 A).

*Fruit stem.*—Moderate in length, approximately 50.0 to about 67.0 millimeters. Diameter — Approximately 2.0 to about 3.0 millimeters. Color — Brown, (approximately RHS Greyed Orange Group 164 C).

*Flesh.*—Rippens — Evenly. Texture — Firm, and dense. Considered melting. Fibers — Few, small, and tender ones are found. Aroma — Slight. Eating Quality — Considered very good. Favor — Considered sweet and sub-acidic. The flavor is viewed as both pleasant and balanced. Juice — Moderate. Brix — About 17.5 degrees. This plant characteristic varies slightly with the number of fruit per tree; the prevailing cultural practices; and the surrounding climatic conditions. Flesh Color — Pale white, (approximately RHS White Group 155 D).

Stone:

*Type.*—Clingstone.

*Size.*—Considered medium-large for the variety. The stone size varies with the resulting crop load, and tree vigor, and is therefore not considered a distinguishing characteristic of this new variety.

*Length.*—Average, about 23.5 to about 25.0 millimeters.

*Width.*—Average, about 21.0 to about 22.0 millimeters.

*Diameter.*—Average, about 17.0 to about 21.0 millimeters.

*Form.*—Obovoid.

*Base.*—The stone base is usually oblique relative to the stone's vertical axis.

*Apex.*—Shape — The stone apex is raised and has an acute, protruding tip.

*Stone surface.*—Surface Texture — This surface texture is characterized by a concentric ridge/furrow pattern which begins at the margins. Substantial grooving over the apical shoulders is evident. Surface pitting is less generally noted than the ridges or furrows, but is more frequently observed in the mid-section of the stone. Substantial erosion is usually observed along the stone margin and near the tip on the ventral side thereof. Ridges — The surface texture varies from sharp to rounded. Ventral Edge — Width — Considered average, and having a dimension of approximately 2.0 to about 4.0 millimeters when measured at the mid-suture. The wings are most prominent over the suture line. Dorsal Edge — Shape — Full, heavily grooved, and having jagged edges.

*Stone color.*—The color of the dry stone is a light brown, (approximately RHS Greyed Orange Group N170 C).

*Tendency to split.*—Occasional splits have been noted.

*Kernel.*—Size — The kernel is considered immature and gelatinous. Form — Considered ovoid. Pellicle — Pubescence. Color — Considered to be a pale brown (Approximately RHS Yellow White Group 158 A).

*Use.*—The subject variety 'Burnectthirteen' is considered to be a Nectarine tree of the early season of maturity, and which produces fruit, which are considered firm, attractively colored, and which are useful for both local and long distance shipping.

*Keeping quality.*—Excellent. Fruit has stored well for up to 25 days after harvest at 1.0 degree Celsius.

*Shipping quality.*—Good. The fruit of the new nectarine tree variety showed minimal bruising of the flesh or skin damage after being subjected to normal harvesting and packing procedures.

*Resistance to insects and disease.*—No particular susceptibilities were noted. The present variety has not been tested to expose or detect any susceptibilities or resistances to any known plant and/or fruit diseases.

Although the new variety of nectarine tree possesses the described characteristics when grown under the ecological conditions prevailing near Fowler, Calif., in the central part of the San Joaquin Valley of California, it should be understood that variations of the usual magnitude and characteristics incident to changes in growing conditions, fertilization, pruning, pest control and horticultural management are to be expected.

Having thus described and illustrated our new variety of nectarine tree, what we claim is new and desire to secure by Plant Letters Patent is:

1. A new distinct variety of nectarine tree, substantially as illustrated and described, and which is characterized principally as to novelty by producing an attractively colored white-fleshed, sub-acid clingstone nectarine which is mature for harvesting and shipment approximately May 24 to June 4 under the ecological conditions prevailing in the San Joaquin Valley of Central California.

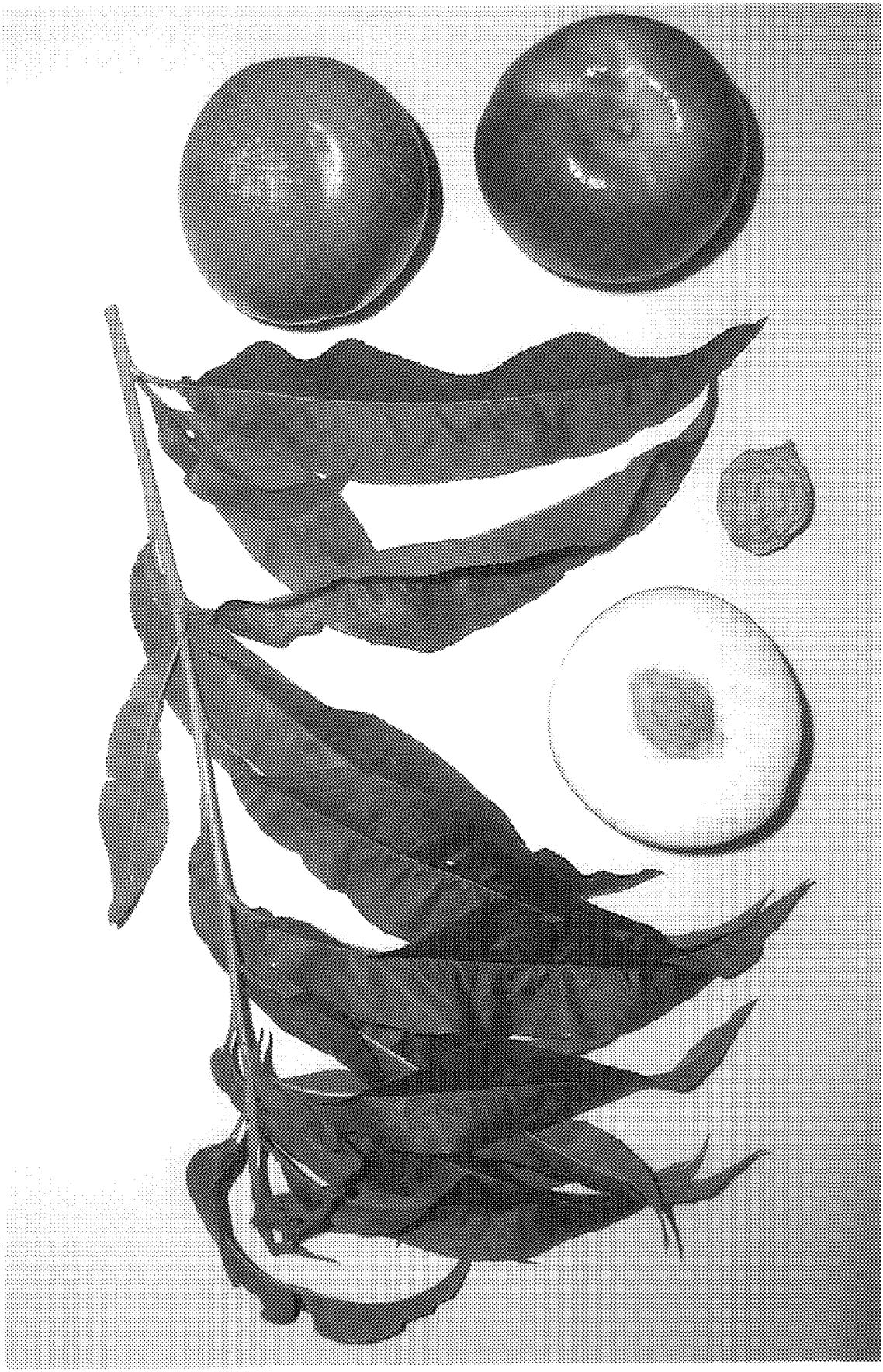

* * * * *